(12) United States Patent
Teoh et al.

(10) Patent No.: US 7,153,323 B1
(45) Date of Patent: Dec. 26, 2006

(54) ANEURYSM LINER WITH MULTI-SEGMENT EXTENDER

(75) Inventors: Clifford Teoh, Los Altos, CA (US); Joseph C. Eder, Los Altos Hills, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 681 days.

(21) Appl. No.: 09/608,781

(22) Filed: Jun. 30, 2000

(51) Int. Cl.
*A61B 17/12* (2006.01)

(52) U.S. Cl. .................. 623/1.23; 623/1.15; 606/158

(58) Field of Classification Search ............... 623/1.15, 623/1.1, 1.11, 1.21, 1.22, 1.32, 1.34, 1.49, 623/1.5, 1.51, 1.54, 920, 921; 606/151, 200, 606/198, 191, 158
See application file for complete search history.

(56) References Cited

U.S. PATENT DOCUMENTS

| | | | |
|---|---|---|---|
| 4,364,392 A | | 12/1982 | Strother et al. |
| 5,250,071 A | * | 10/1993 | Palermo ............. 606/198 |
| 5,334,210 A | * | 8/1994 | Gianturco ........... 606/151 |
| 5,454,833 A | | 10/1995 | Boussignac et al. |
| 5,782,860 A | | 7/1998 | Epstein et al. |
| 5,916,235 A | * | 6/1999 | Guglielmi ........... 606/200 |
| 5,928,260 A | * | 7/1999 | Chin et al. ......... 606/200 |
| 5,976,174 A | | 11/1999 | Ruiz |
| 6,096,034 A | * | 8/2000 | Kupiecki et al. ..... 606/32 |
| 6,168,592 B1 | * | 1/2001 | Kupiecki et al. ..... 606/32 |
| 6,344,041 B1 | * | 2/2002 | Kupiecki et al. ..... 606/32 |
| 6,350,270 B1 | * | 2/2002 | Roue .................. 606/151 |
| 6,383,174 B1 | * | 5/2002 | Eder .................. 606/1 |

FOREIGN PATENT DOCUMENTS

| | | |
|---|---|---|
| EP | 0 711 532 A1 | 5/1996 |
| WO | WO94/06503 | 3/1994 |
| WO | WO 96/01591 | 1/1996 |
| WO | WO99/03404 | 1/1999 |
| WO | WO 99/30640 | 6/1999 |
| WO | WO99/42059 | 8/1999 |

OTHER PUBLICATIONS

U.S. patent application Ser. No. 09/490,788, Roue, filed Jan. 2000.
International Search Report of PCT Application No. PCT/US01/19669 of SciMed Life Systems, Inc.

* cited by examiner

*Primary Examiner*—Gloria M. Hale
(74) *Attorney, Agent, or Firm*—Bingham McCutchen LLP

(57) ABSTRACT

A device for treating an aneurysm including an aneurysm liner expandable to form an inner cavity and a plurality of extender segments supported in the aneurysm liner. The device includes an axial constraint coupled to the plurality of extender segments in the liner to axially constrain extender segments in end to end alignment to bias the liner in a collapsed profile.

23 Claims, 7 Drawing Sheets

ANEURYSM LINER WITH MULTI-SEGMENT EXTENDER

BACKGROUND OF THE INVENTION

The present invention relates to a device for treating an aneurysm. More specially, the present invention relates to an aneurysm liner expandable from a collapsed profile for deployment in an aneurysm sac.

An aneurysm is a localized stretching or distension of a vessel due to a weakening of the vessel wall. For example, "berry" aneurysms, i.e., small spherical distensions, occur in the vessels of the brain. The distensions—often referred to as the aneurysm sac—are related to defects on the muscular coating of the artery or vessel and are probably degenerative in origin. Rupture of aneurysms accounts for the majority of the spontaneous hemorrhages. Approximately 25,000 intracranial aneurysms rupture every year in North America.

Several methods for treating aneurysms have been attempted, with varying degrees of success. At present, the treatment of aneurysms with drugs is substantially ineffective. Also, extra-vascular surgery, referred to as open craniotomy, for the purpose of preserving the parent artery is replete with disadvantages. A patient subject to open craniotomy for intercranial aneurysms typically must undergo general anesthesia, surgical removal of part of the skull, brain retraction, dissection around the neck of the sac, and placement of a clip on the parent artery to prevent bleeding or rebleeding.

Alternative treatments include endovascular occlusion where the interior of the aneurysm is entered with a guidewire or a microcatheter. An occlusion is formed within the sac with an intention to preserve the parent artery. A preferred means for forming a mass in an aneurysm sac is through the introduction of an embolic agent within the sac. Examples of embolic agents include a detachable coil, which is detached from the end of a guidewire, and a liquid polymer which polymerizes rapidly on contact with blood to form a firm mass. Endovascular occlusion is not without drawbacks. For example, there is a risk of overfilling the sac which can cause embolic agent to migrate from the aneurysm sac into the parent vessel and can create additional pressure in the aneurysm.

Another means for forming a mass in the aneurysm sac involves the placement of an expandable balloon or liner in the aneurysm. Detachable occlusion balloons have been used for a number of medical procedures. These balloons are carried at the end of a and, once inflated can be detached from the catheter. Such a balloon may be positioned within an aneurysm, filled and then detached from the catheter. Deploying an expandable balloon within the aneurysm can be rather difficult due to the high rates of blood flow through the aneurysm.

The balloon must be sufficiently inflated to fill the aneurysm so that it does not migrate from the aneurysm sac but not over inflated because an overinflated balloon can rupture or can put undue pressure on the aneurysm walls. Furthermore, the balloon often does not mold or shape to the odd-shaped contours of the aneurysm leaving room for blood to continue flowing through the aneurysm. Elastic balloons have exhibited problems with respect to performance and have not been used endovascularly in some time.

Aneurysm liners are composed of a liner sac which is placed in the aneurysm and filled to occlude the aneurysm. Aneurysm liners are formed of a semi-permeable fabric and are expanded to conform to the shape of the aneurysm. Aneurysm liners are inserted in a low profile into an aneurysm sac. Once inserted, the liner can be radially expanded to form an inner cavity in the liner. The liner is radially expanded by filling the liner with embolic material. The liner can be attached to a catheter device to insert and deploy the liner in the aneurysm sac. The aneurysm liner is inserted intravascularly over a guidewire extending through a lumen in the liner. In such devices, the guidewire lumen should not form a passage for embolic material through the liner, since passage of embolic material through the liner can hinder the process of filling the liner with embolic material to occlude the aneurysm. The present invention addresses these and other problems.

SUMMARY OF THE INVENTION

The present invention relates to a device for treating an aneurysm including an aneurysm liner expandable to form an inner cavity and a plurality of extender segments supported in the aneurysm liner. The device includes an axial constraint coupled to the plurality of extender segments in the liner to axially constrain extender segments in end to end alignment to bias the liner in a collapsed profile.

DETAILED DESCRIPTION OF THE ILLUSTRATIVE EMBODIMENTS

Figure 1:
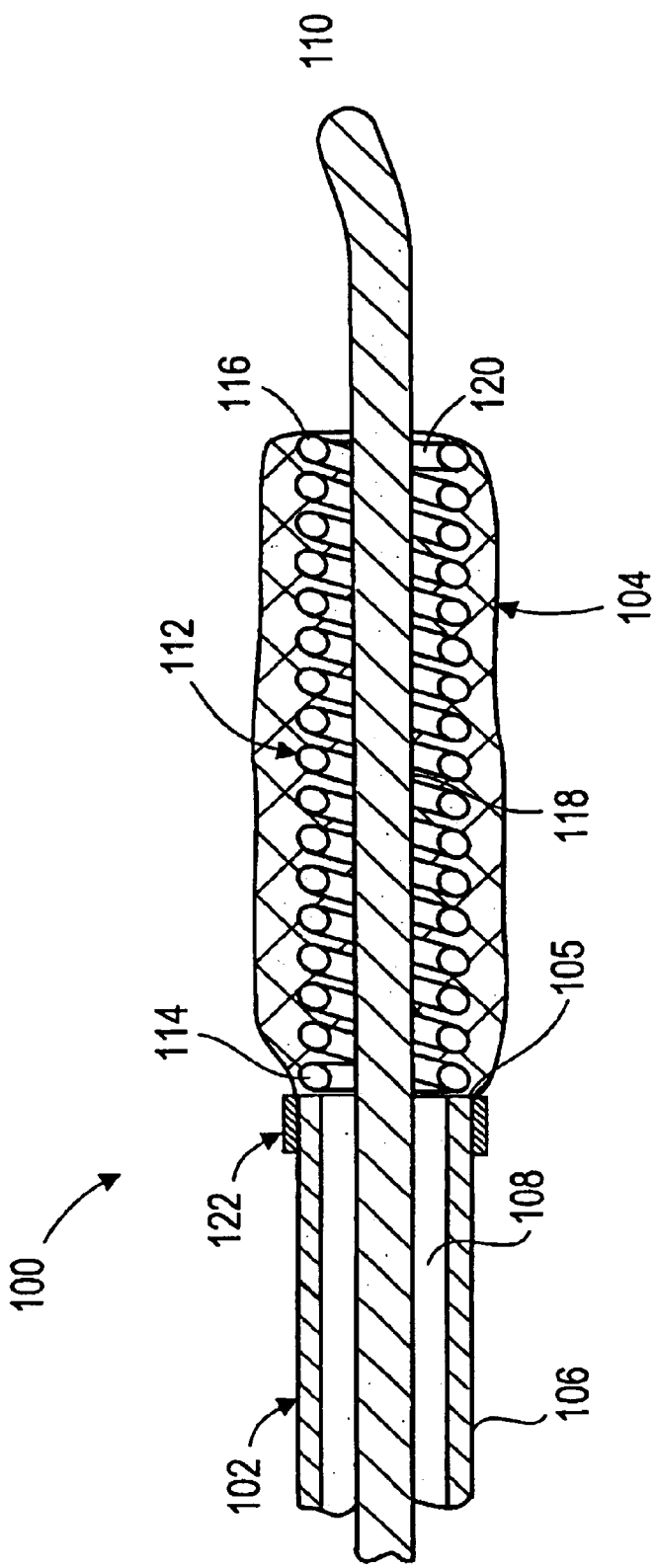
FIG. 1 is an illustrative view of a device including an aneurysm liner in a collapsed profile.

FIG. 1 is, an embodiment of an aneurysm treatment device 100. Device 100 includes an elongated flexible catheter 102 and an expandable aneurysm liner 104. Flexible catheter 102 includes a proximal end (not shown in FIG. 1), a distal end 105 and elongated length extending therebetween. Expandable aneurysm liner 104 is supported proximate to the distal end 105 of the flexible catheter and is operable between a collapsed profile shown in FIG. 1 and an expanded deployed profile as will be explained.

In the embodiment of FIG. 1, catheter 102 includes an elongated catheter shaft 106 and guidewire lumen 108. A guidewire 110 extends through the guidewire lumen 108 for tracking and advancing catheter 102 to a treatment site. Aneurysm liner 104 is retained in a collapsed profile for insertion by an extender 112. The extender 112 in FIG. 1 is formed of a flexible elongated tubular shaped member having a proximal end 114 and distal end 116 and a channel 118 extending therethrough. Extender 112 is aligned so that channel 118 forms a guidewire lumen extending through liner 104 and a distal opening 120 of the liner 104 is formed about channel 118. As shown guidewire 110 extends through channel 118 to axially constrain extender 112 to collapse liner 104 for insertion.

As shown, the proximal end 114 of the axially constrained extender 112 abuts a proximal end of the catheter shaft and the distal end 116 of the axially constrained extender 112 abuts a distal end of liner 104 to bias the liner 104 in a collapsed profile shown. As shown in FIG. 1, the proximal end of liner 104 is detachable connected about a distal end of catheter shaft 106. Liner 104 is detachable connected to catheter shaft 106 as illustrated at 122 with a suitable technique such as a Guglielm detachment mechanism, a conductive adhesive, or other temporary connection.

Figure 2:
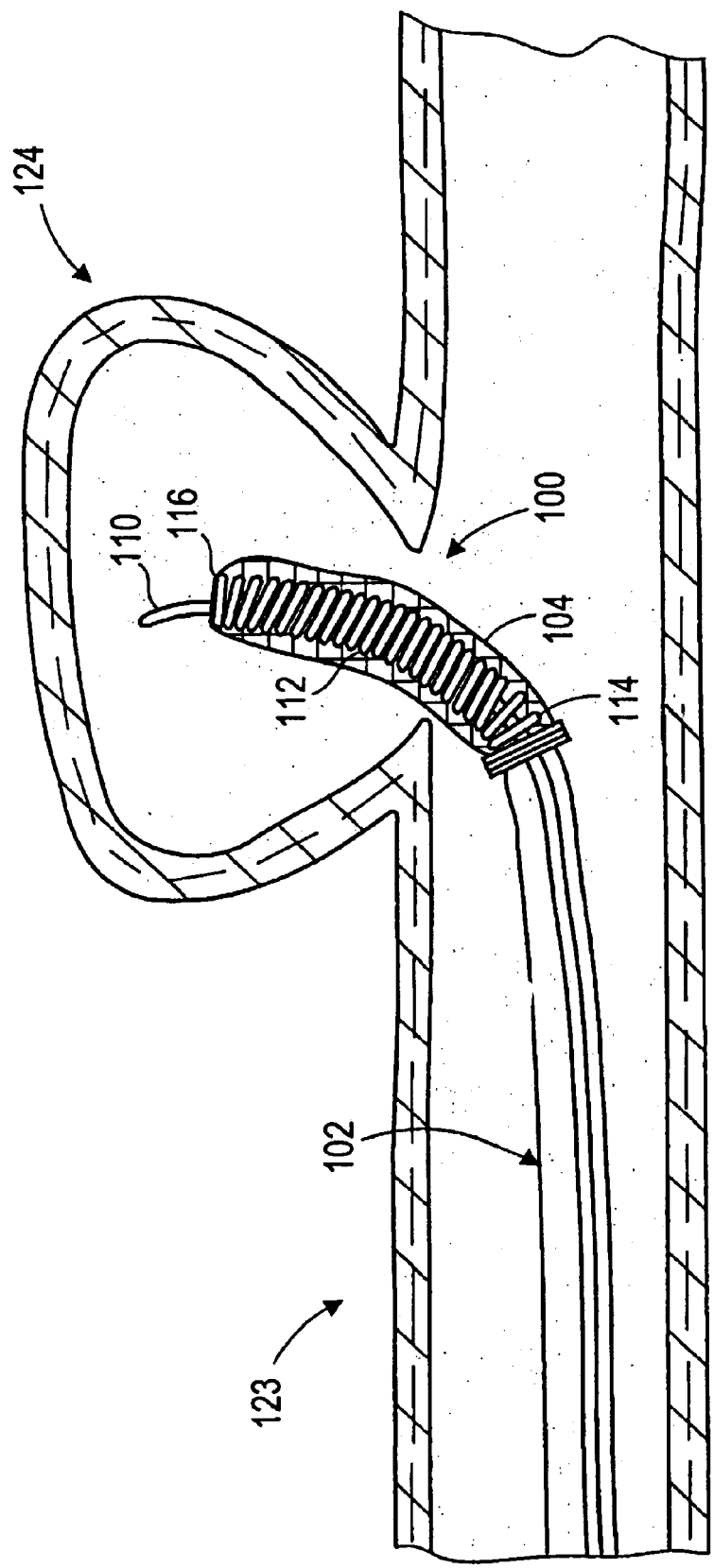
FIG. 2 schematically illustrates intravascular insertion and placement of the aneurysm liner of FIG. 1 in an aneurysm sac.

As shown in FIG. 2, device 100 is inserted over guidewire 110 through a vascular lumen 123 or other body lumen into an aneurysm sac 124. Guidewire 110 helps navigate the catheter 102 through the vascular lumen 123 or other body vessel to insert liner 104 into the sac 124. The length of the axially constrained extender 112 between proximal and distal ends 114, 116 is sufficient to collapse the profile of the liner 104 so that the liner 104 can be intravascularly navigated into the aneurysm sac 124. Once positioned in the aneurysm sac 124, extender 112 is released from its constrained alignment to allow the liner 104 to expand to form an inner cavity. As shown in FIG. 1, extender 112 is formed of a flexible coil so that once released from its axial constrained alignment, the coil will bend or flex from its axially aligned position to allow the liner 104 to radially expand. The extender 112 is released from its constrained alignment by withdrawing the guidewire from the channel 118 so that guidewire 110 no longer axially constrains extender and the liner 104 can radially expand for deployment in the aneurysm sac 124.

Figure 3:
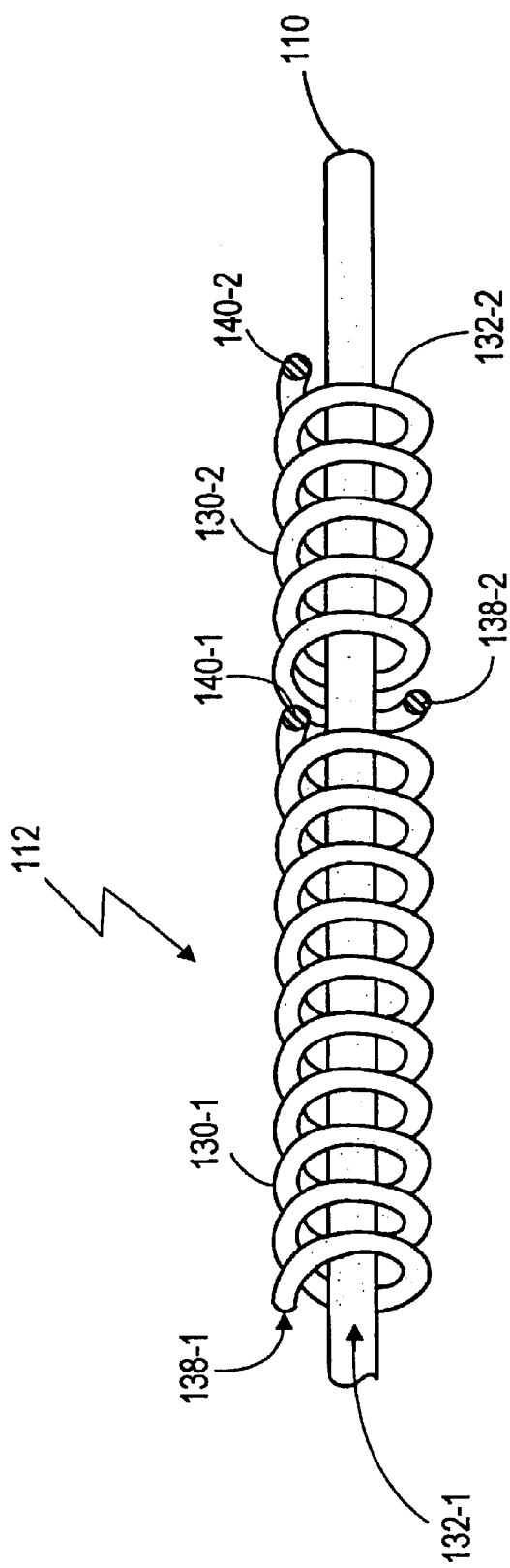
FIG. 3 is an illustration of an aneurysm liner including an embodiment of a multi-segment extender in an unconstrained position to radially deploy the liner.
Figure 4:
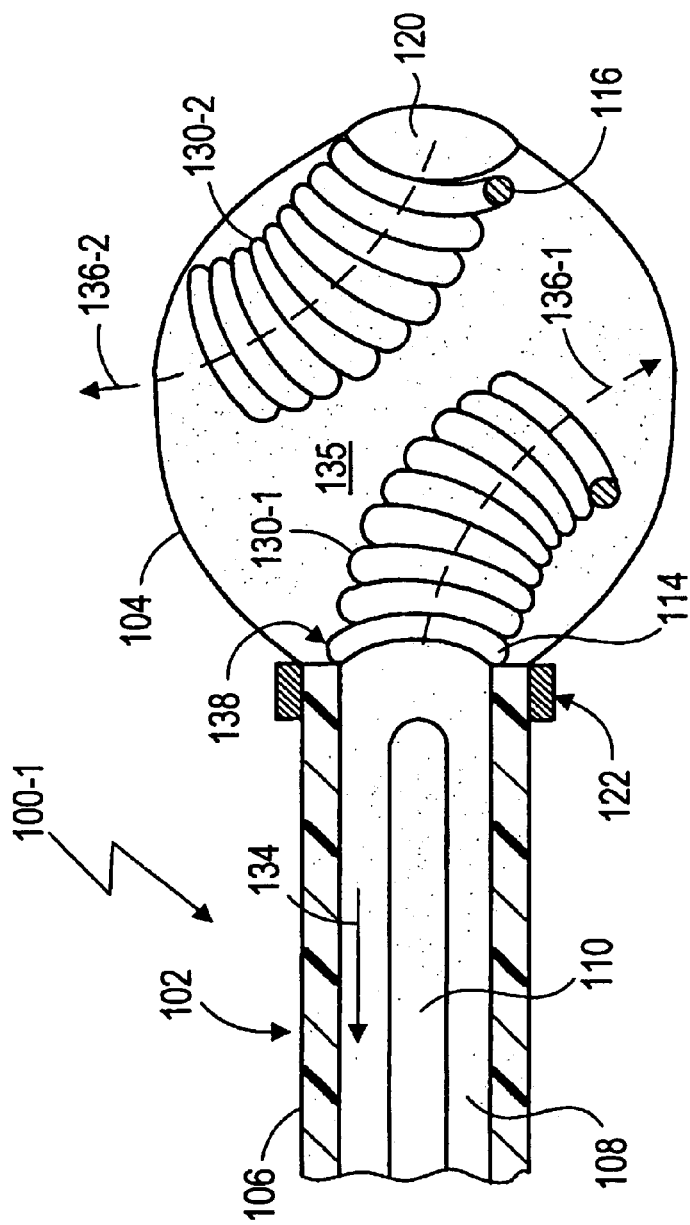
FIG. 4 is an illustration of the embodiment of the multi-segment extender of FIG. 3 for collapsing an aneurysm liner for insertion.

FIGS. 3–4 illustrate an embodiment of an aneurysm device 100-1 of the present invention where like numbers are used to refer to like parts in the previous FIGS. As shown, extender 112 includes tubular extender segments 130-1, 130-2 which are axially constraint in end to end relation as shown in FIG. 4 to form an elongated extender 112 having sufficient length to axially collapse the liner 104. Extender segments 103-1, 103-2 include segment channels 132-1, 132-2 and in the embodiment shown extender segments 130-1, 130-2 are axially constrained by guidewire 110 extending through segment channels 132-1, 132-2. The axial constrained extender segments 130-1, 130-2 provide an axial force at opposed ends of liner 104 to bias liner 104 in a collapsed profile as shown in FIG. 1 and channels 132-1, 132-2 cooperatively form a guidewire lumen through liner 104 to protect liner 104 from damage from the guidewire 110.

For deployment of the liner 104, guidewire is proximally withdrawn as illustrated by arrow 134 in FIG. 3 to release the axially constrained segments 130-1, 130-2 so that the segments 130-1, 130-2 and liner 104 are unconstrained. The unconstrained segments 130-1, 130-2 bend, flex or shift from the axially constrained alignment to allow the collapsed liner 104 to radially expand to form an inner cavity 135. The unconstrained liner 104 is expanded inter alia by filling the liner with embolic material as will be explained. The liner 104 can be formed of woven, braided or fine knitted fabric of a semi-permeable biocompatible material such as a DACRON® material, Nylon, LYCRA®, or a TEFLON® material. DACRON®, LYCRA® and TEFLON® are registered trademarks of E.I. du Pont de Nemours and Company of Wilmington, Del. The knit, braid or weave is dense enough to resist penetration from embolic coils and strong enough to contain embolic coils.

In the embodiment illustrated in FIGS. 3–4, extender segments 130-1, 130-2 have a preformed shape with extender segment 130-1 biased in a first direction and extender segment 130-2 biased in a second direction so that once guidewire 110 is withdrawn, extender segment 130-1 flexes or coils in a first direction illustrated by arrow 136-1 and extender segment 130-2 flexes or coils in a second opposed direction as illustrated by arrow 136-2. The opposed bias of the extender segments 130-1, 130-2 facilitates separation of extender segments 130-1, 130-2 to assure that the axial force collapsing the liner is completely released. The flexure of the extender segments 130-1, 130-2 can impart an expansion force to radially deploy the liner 104 as shown in FIG. 3. The opposed bias of extender segments 130-1, 130-2 also assures that the segments 130-1, 130-2 separate so that channels 132-1, 132-2 do not form a continuous lumen through the unconstrained liner 104 as will be explained.

In the embodiment illustrated in FIG. 4, extender segments 130-1, 130-2 are formed of a helical coil. In one embodiment, flexible helical coil segments are made of a stainless steel or radiopaque material (such as platinum). Alternatively, coil segments could be formed of a polymer material having sufficient rigidity to stretch the liner to a collapsed profile. The length of the axially constrained extender segments 130-1, 130-2 can be sized to stretch the liner 104 to a collapsed profile or the length of the axially constrained extender segments 130-1, 130-2 can be sized similar to a length of the liner 104 to collapse the liner without significant stretching.

In one embodiment, a proximal end 138-1 of extender segment 130-1 is permanent or detachably connected to the distal end of the catheter shaft 106 and a distal end 140-1 of extender segment 130-1 is "free" or unattached. A distal end 140-2 of extender segment 130-2 is permanently or detachable connected to the liner 104 while proximal end 138-2 of extender segment 130-2 is "free" or unattached. Although in the embodiment described, the proximal end 138-1 and distal end 140-2 of extender segments 130-1, 130-2, respectively are attached to the catheter shaft or liner 104, the proximal end and distal ends of either extender segments 130-1, 130-2 can be attached or unattached to the liner 104 or catheter 102. Various methods of permanent attaching extender segments to liner 104 can be used such as sewing, threading coil into a weave of liner 104, ultrasonic bonding, crimping, marker bands, adhesives or other known methods.

Figure 5:
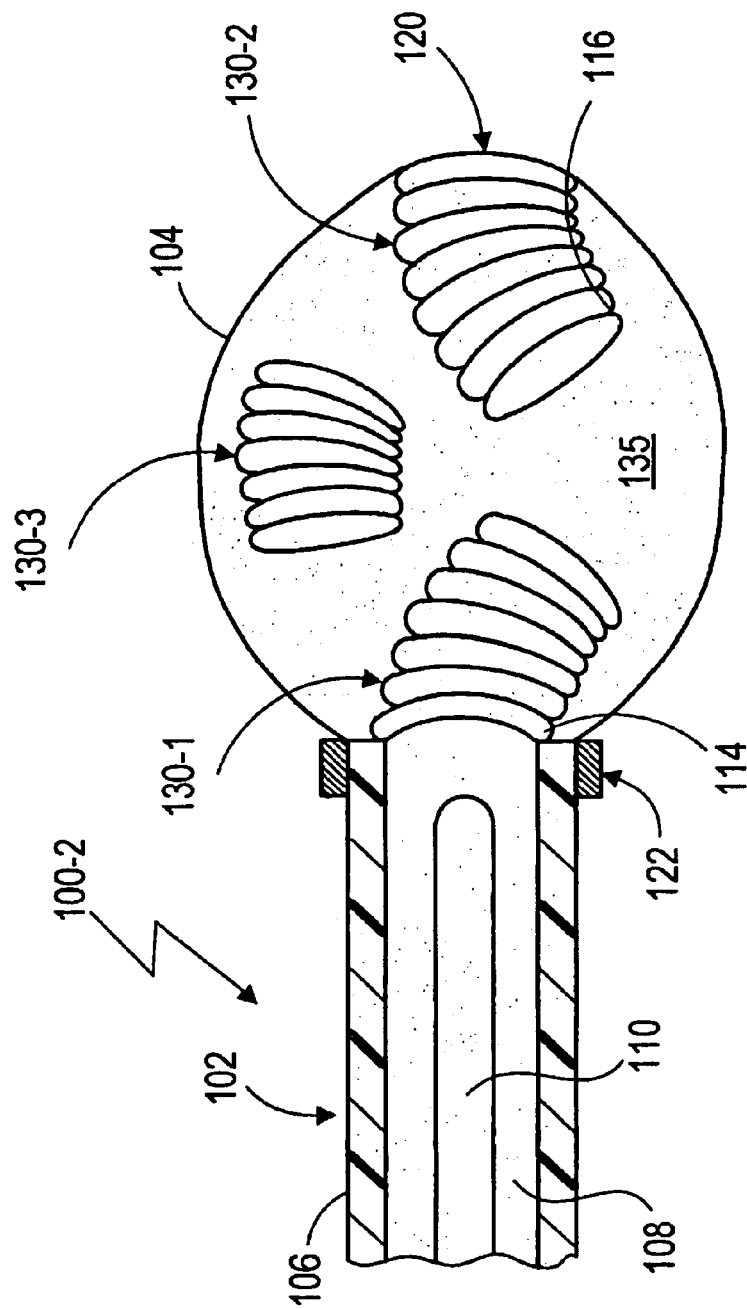
FIG. 5 is an illustration of an aneurysm liner including another embodiment of a multi-segment extender in an unconstrained position to radially deploy the liner.
Figure 6:
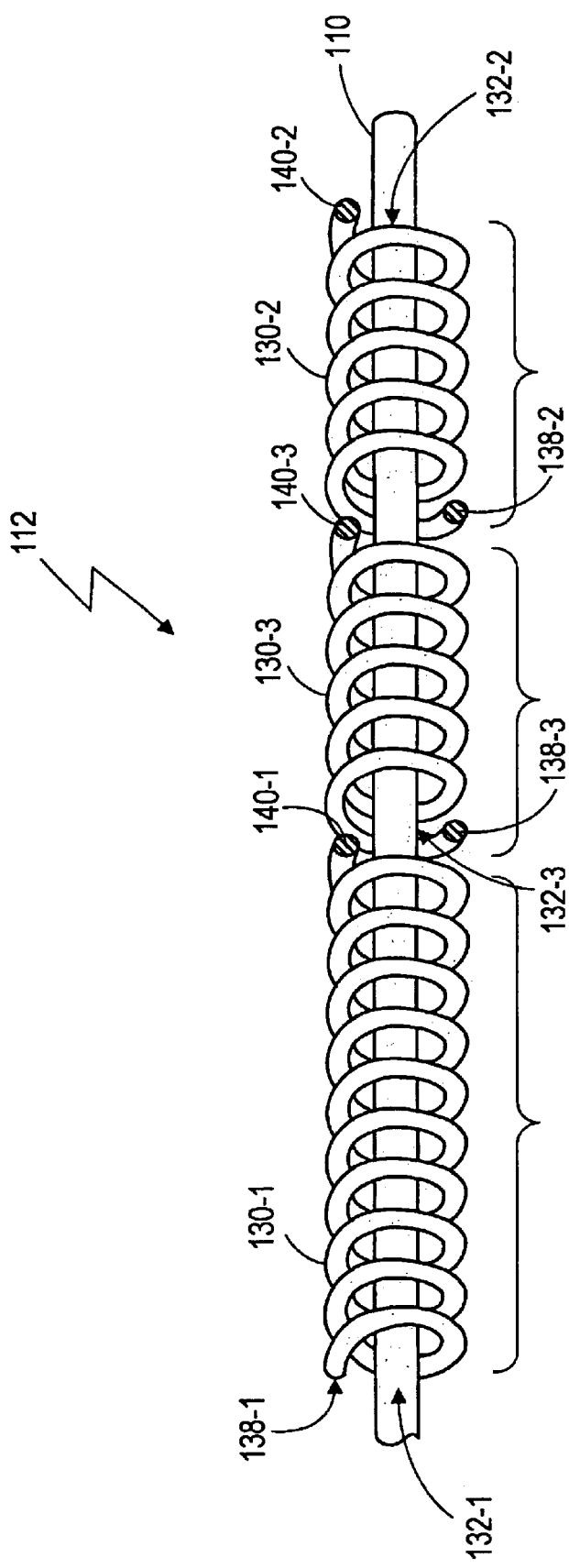
FIG. 6 is an illustration of the embodiment of the multi-segment extender of FIG. 5 for collapsing an aneurysm liner for insertion.

FIGS. 5–6 illustrate another embodiment of an aneurysm device 100-2 of the present invention, where like numbers are used to refer to like parts in the previous FIGS. In the embodiment shown, extender 112, includes tubular extender segments 130-1, 130-2 and 130-3. Extender segments 130-1, 130-2 form proximal and distal extender segments and extender segment 130-3 is interposed between extender segments 130-1, 130-2 to form a floating extender segment. Extender segments 130-1, 130-2, 130-3 include channels 132-1, 132-2, 132-3, respectively.

In the embodiment illustrated in FIG. 6, extender segments 130-1, 130-2, 130-3 are axially; constrained in end to end relation by guidewire 110 extending through channels 132-1, 132-2 132-3. As previously discussed, the axial constrained spring segments 130-1, 130-2, 130-3 provide an axial force to opposed ends of the liner 104 to collapse the profile of liner 104 for insertion. Device 100-2 is introduced over guidewire 110 and channels 132-1, 132-2, 132-3 of extender segments 130-1, 130-2, 130-3 cooperatively form a portion of the guidewire lumen extending through liner 104 to protect liner 104 from damage from the guidewire 110.

Guidewire 100 extends through extender segments 130-1, 130-2, 130-3 to track device 100-2 to a treatment site and to axially constrain liner 104 in a low profile for insertion. As previously discussed in relation to FIGS. 3–4, guidewire 110 is withdrawn to release the axially constrained extender segments 130-1, 130-2, 130-3 so that the extender segments 130-1, 130-2, 130-3 and liner 104 are unconstrained to radially deploy liner 104.

Figure 7:
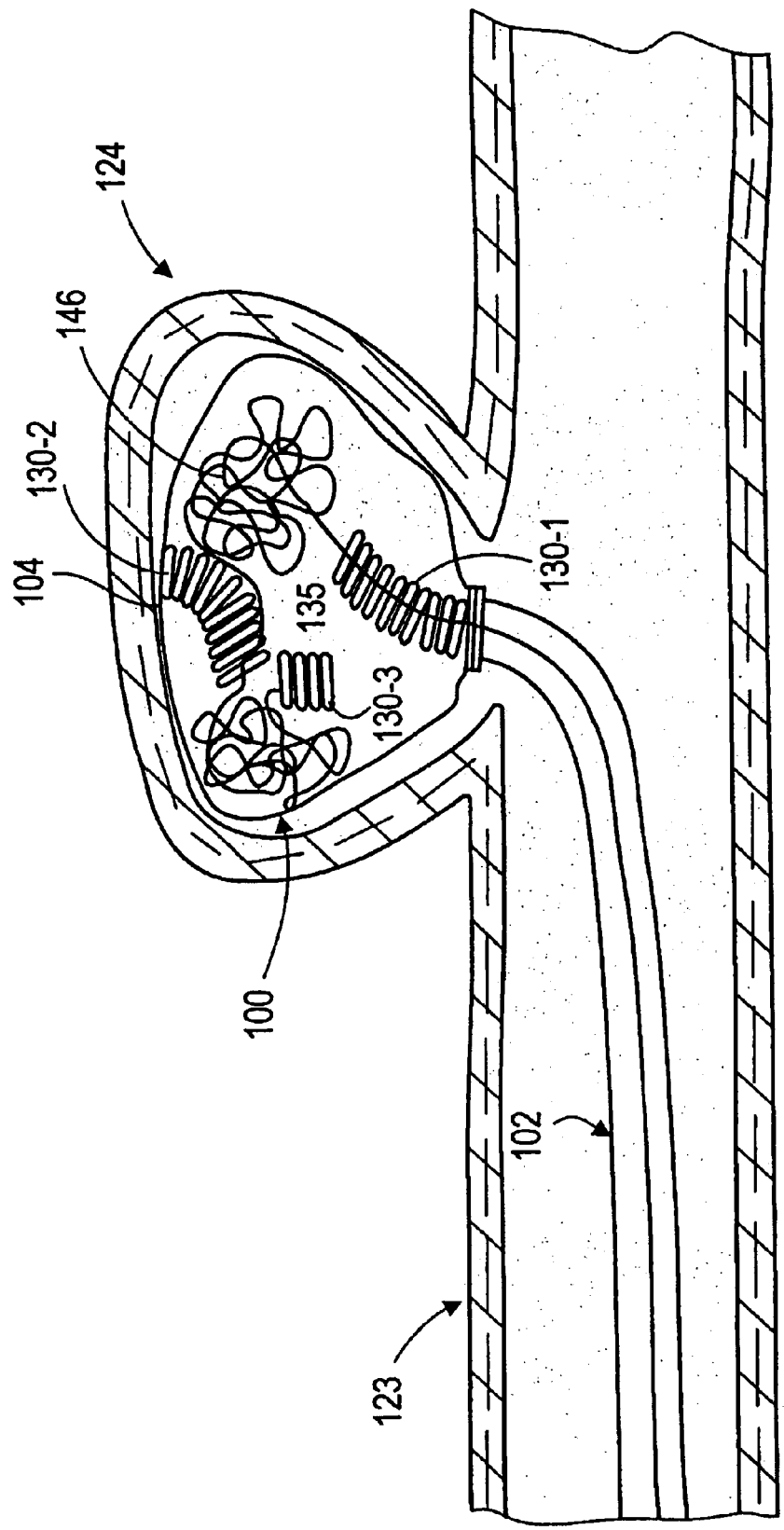
FIG. 7 is an illustration of a deployed aneurysm liner including the multi-segment extender of FIGS. 5–6 and having embolic coils inserted into a cavity of the aneurysm liner.

In the embodiment shown, a proximal end 138-1 of segment 130-1 is connected to shaft 106 and a distal end 140-1 of segment 130-1 is "free". A distal end 1402 of segment 130-2 is connected to liner 104 and the proximal end 138-2 is "free". Both ends of segment 13025 3 are free to form a "floating" segment between segments 130-1, 130-2. Multiple extender segments 130-1, 130-2, 130-3 facilitates release of the axial force constraining liner 104 in a low profile to facilitate radial expansion of liner 104 as shown in FIG. 7. The multiple extender segments 130-3 also facilitate disintegration of the channel segments 132-1, 130-2, 132-3 forming the guidewire lumen through the liner 104 for insertion of embolic material into the inner cavity 135 of the liner.

Although FIGS. 3–6, illustrate coil extender segments 130-1, 130-2, 130-3, application of the present invention is not limited to the specific embodiments shown and the extender segments 130-1, 130-2, 130-3 can be formed of other designs which are axially constrained in end to end alignment to collapse the profile of the liner 104. To radially expand the liner 104, the segments 130-1, 130-2, 130-3 are released from the constrained axial end to end alignment to allow the liner to expand from the collapsed profile. For example, extender segments 130-1, 130-2, 130-3 can be formed of a plurality of cylindrical tubes constructed of a polymer material or other compatible material which are axially aligned to collapse the liner and which are released from the axial alignment to radially expand the liner 104.

As shown in FIG. 7, once the axial constraint is released, embolic material 146 can be introduced into the unconstrained liner 104 to radially expand the liner 104. For example, embolic coils can be introduced through catheter 102 (guidewire lumen 108) into an inner cavity 135 of the liner 104. For example, embolic coils or particles can be injected, infused or advanced through the guidewire lumen 108 with the guidewire 110 withdrawn. Once the liner 104 is filled, it is unable to migrate out of the aneurysm sac 124 and liner 104 can then be detached from catheter 102 and the catheter withdrawn from the patient. As generally illustrated in FIG. 7, the liner 104 is formed so that the liner 104 has no predetermined shape and thus, can fill any given aneurysm sac 124 without exerting unwanted pressure on the walls of the aneurysm.

In the device of the present invention the guidewire lumen through liner 104 is formed by the multi axially constrained segments having multi channel segments. For insertion and placement of the device into an aneurysm sac 124, it is desirable that the channel segments form a guidewire lumen through liner 104 to advance liner 104 and device 100 over guidewire 110. However, to fill the liner, catheter lumen must be open to the interior cavity 135 of liner 104. If in the unconstrained liner 104, channel segments 132 form a guidewire lumen open to the distal opening 120, the lumen forms a passage for embolic material through the liner. Passage of embolic material through the liner interferes with filling the liner to radially expand the liner to occlude the aneurysm.

The multi extender segments of the present invention facilitate disintegration of the guidewire lumen in the unconstrained liner 104 to fill the liner 104 with embolic material for deployment. Once liner 104 is filled, it is released from the catheter 102 and the catheter 102 is removed from the patient. The filled liner cannot be removed from the sac 124 without removing the embolic material from the inner cavity 135 of the liner 104.

As previously described, proximal segment 1301 and distal segments 130-2 can be connected to the catheter and liner 104, respectively. In the embodiment described, embolic material 146 can be inserted through the proximal segment 130-1 attached to catheter 102 into the cavity of the liner 104. Insertion of the embolic material through proximal segment 130-1 advances material into a center portion of liner 104 to facilitate insertion of material into the entire cavity volume. Alternatively, proximal and distal segments 130-1, 130-2 can have floating ends which are not attached to the catheter or liner 104, respectively.

Thus, as described, the aneurysm device including multi extender segments provides a reliable device for collapsing an aneurysm liner and forming a guidewire lumen for inserting the liner over a guidewire. The multi-extender segments facilitate expansion of the liner and disintegration of the guidewire lumen through the unconstrained liner to fill the liner with embolic material.

Although the present invention has been described with reference to preferred embodiments, workers skilled in the art will recognize that changes may be made in form and detail without departing from the spirit and scope of the invention.

What is claimed is:

1. A device for treating an aneurysm comprising:
   an elongated flexible catheter having a guidewire lumen;
   an aneurysm liner having a proximal end coupled to the distal end of the flexible catheter and expandable to form an inner cavity;
   a plurality of tubular extender segments supported in the aneurysm liner; and
   a guidewire extendable through the tubular extender segments to constrain the plurality of extender segments to support the aneurysm liner in a collapsed profile.

2. The device of claim 1 wherein the tubular extender segments are formed of flexible coil segments.

3. The device of claim 1 wherein the tubular extender segments are preformed so that in an unconstrained condition, the plurality of extender segments curve in opposed directions to separate unconstrained extender segments to disintegrate a guidewire lumen formed through the plurality of constrained extender segments.

4. The device of claim 1 wherein one of the plurality of extender segments is connected to the flexible catheter.

5. The device of claim 1 wherein one the plurality of extender segments is connected to the aneurysm liner.

6. The device of claim 1 wherein the expandable aneurysm liner includes a distal liner opening and constrained tubular expander segments form a guidewire lumen opened to the distal lumen opening.

7. The device of claim 1 wherein the aneurysm liner is detachable coupled to the catheter.

8. A device for treating an aneurysm comprising:
   an aneurysm liner expandable to form an inner cavity;

a plurality of extender segments; and a constraint coupled to the plurality of extender segments to constrain the extender segments in end to end alignment to bias the aneurysm liner in a collapsed profile.

9. The device of claim 8 wherein the plurality of extender segments are formed of tubular segments and the constraint is an elongated wire extending through channels of the tubular segments.

10. The device of claim 8 wherein the plurality of extender segments are formed of coil segments.

11. The device of claim 8 wherein the plurality of extender segments includes proximal and distal extender segments and at least one intermediate extender segment.

12. The device of claim 8 wherein a length of the constrained extender segments is sized to stretch the aneurysm liner to bias the aneurysm liner in the collapsed profile.

13. The device of claim 8 wherein a length of constrained extender segments is approximately equal to an axial length of the aneurysm liner to bias the aneurysm liner in the collapsed profile.

14. The device of claim 8 wherein at least one of the plurality of extender segments is floatably supported in the expandable aneurysm liner.

15. A device for treating an aneurysm comprising:

an elongated flexible catheter having a guidewire lumen;

an aneurysm liner expandable to form an inner cavity, and the aneurysm liner having a proximal end coupled to a distal end of the flexible catheter, and a distal end having a distal opening; and a plurality of tubular extender segments supported in the aneurysm liner to support the aneurysm liner between a collapsed constrained condition and an expanded unconstrained condition and in the constrained condition the plurality of extender segments cooperatively forming a guidewire lumen opened to the distal opening and in the unconstrained condition, the formed guidewire lumen disintegrating.

16. A method for treating an aneurysm comprising steps of:

endovascularly inserting an aneurysm liner supported in a collapsed profile by a plurality of constrained extender segments, into an aneurysm sac; and releasing the constraint of the plurality of extender segments to deploy the aneurysm liner.

17. The method of claim 16, further comprising the step of:

inserting embolic material into an inner cavity of the aneurysm liner to radially expand the aneurysm liner.

18. The method of claim 16 wherein the aneurysm liner is coupled to a catheter having a guidewire lumen and the extender segments include tubular segments which cooperatively form a guidewire lumen extending through the aneurysm liner and the step of endovascularly inserting the aneurysm liner comprising the step of:

advancing the catheter and the aneurysm liner over a guidewire into the aneurysm sac.

19. The method of claim 16 wherein the aneurysm liner is detachable connected to an elongated flexible catheter and comprising steps of:

intravascularly inserting the catheter to insert the aneurysm liner into the aneurysm sac; and detaching the catheter from the deployed aneurysm liner and withdrawing the catheter.

20. The method of claim 19 wherein prior to detaching the catheter comprising the step of:

inserting embolic material through the catheter into an inner cavity of the aneurysm liner to radially expand the aneurysm liner.

21. The method of claim 16 wherein the plurality of extender segments are constrained by a guidewire extending through tubular channels of the plurality of extender segments and the step of releasing the constrained extender segments comprises:

withdrawing the guidewire from the tubular channels of the plurality of extender segments.

22. A device for treating an aneurysm comprising:

an expandable aneurysm liner having an inner cavity;

a plurality of tubular extender segments; and means for selectively constraining and releasing the plurality of tubular extender segments to selectively collapse the aneurysm liner and form a lumen through the collapsed aneurysm liner and release the aneurysm liner from a constraint of the plurality of tubular extender segments and disintegrate the lumen through the aneurysm liner.

23. The device of claim 13 wherein the aneurysm liner is detachably coupled to the catheter.

* * * * *